US007927479B2

(12) United States Patent
Greaney et al.

(10) Patent No.: US 7,927,479 B2
(45) Date of Patent: Apr. 19, 2011

(54) FOCUSED BEAM REFLECTANCE MEASUREMENT TO OPTIMIZE DESALTER PERFORMANCE AND REDUCE DOWNSTREAM FOULING

(75) Inventors: Mark A. Greaney, Upper Black Eddy, PA (US); Glen B. Brons, Phillipsburg, NJ (US); Chris A. Wright, Bordentown, NJ (US); Daniel P. Leta, Flemington, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 1154 days.

(21) Appl. No.: 11/641,753

(22) Filed: Dec. 20, 2006

(65) Prior Publication Data

US 2008/0149486 A1 Jun. 26, 2008

(51) Int. Cl.
*G01N 33/00* (2006.01)

(52) U.S. Cl. ............ 208/47; 208/187; 208/309; 436/40

(58) Field of Classification Search .................... 208/47, 208/48 R, 87, 251 R; 204/570, 571; 210/695, 210/702, 708
See application file for complete search history.

(56) References Cited

U.S. PATENT DOCUMENTS

| | | | | |
|---|---|---|---|---|
| 4,581,134 | A | 4/1986 | Richter, Jr. et al. | |
| 4,947,885 | A | 8/1990 | Hart | |
| 4,985,696 | A | 1/1991 | Beomont | |
| 5,619,043 | A * | 4/1997 | Preikschat et al. | 250/574 |
| 5,734,098 | A | 3/1998 | Kraus et al. | |
| 6,428,669 | B2 | 8/2002 | Klippel et al. | |
| 6,838,006 | B2 | 1/2005 | Feierabend et al. | |
| 7,244,364 | B1 | 7/2007 | Weber | |
| 2002/0033356 | A1 | 3/2002 | Honda et al. | |
| 2002/0157991 | A1 * | 10/2002 | Mason et al. | 208/255 |

FOREIGN PATENT DOCUMENTS

| | | |
|---|---|---|
| FR | 2 315 534 | 1/1977 |
| FR | 2 388 037 | 11/1978 |
| FR | 2 864 239 | 6/2005 |
| GB | 1 497 610 | 1/1978 |
| WO | WO 89/04725 | 6/1989 |
| WO | WO 95/12118 | 5/1995 |
| WO | WO 00/46586 | 8/2000 |

OTHER PUBLICATIONS

Partial International Search Report, PCT/US2007/025821, mailed Jun. 26, 2008.

* cited by examiner

*Primary Examiner* — Walter D Griffin
*Assistant Examiner* — Brian McCaig
(74) *Attorney, Agent, or Firm* — Malcolm D. Keen; Glenn T. Barrett

(57) ABSTRACT

Performance of equipment, such as a desalter, in a refinery is monitored in real-time and on-line to minimize fouling of downstream equipment. Using an instrument to measure particles and droplets in-process allows monitoring of the various operations to optimize performance. Such measurement can also be used during crude oil blending to detect asphaltene precipitates that can cause fouling and can be used for monitoring other fouling streams.

19 Claims, 3 Drawing Sheets

FOCUSED BEAM REFLECTANCE MEASUREMENT TO OPTIMIZE DESALTER PERFORMANCE AND REDUCE DOWNSTREAM FOULING

BACKGROUND OF THE INVENTION

1. Field of the Invention

This invention relates to processing of whole crude oils, blends and fractions in refineries and petrochemical plants. In particular, this invention relates to monitoring performance of components in a refinery, especially monitoring performance of a desalter. This invention also relates to optimizing a refinery operation to mitigate fouling.

2. Discussion of Related Art

Fouling is generally defined as the accumulation of unwanted materials on the surfaces of processing equipment. In petroleum processing, fouling is the accumulation of unwanted hydrocarbon-based deposits on heat exchanger surfaces. These deposits often include inorganic materials as well. It has been recognized as a nearly universal problem in design and operation of refining and petrochemical processing systems, and affects the operation of equipment in two ways. First, the fouling layer has a low thermal conductivity. This increases the resistance to heat transfer and reduces the effectiveness of the heat exchangers. Second, as deposition occurs, the cross-sectional area is reduced, which causes an increase in pressure drop across the apparatus.

Fouling in heat exchangers associated with petroleum type streams can result from a number of mechanisms including chemical reactions, corrosion, deposit of insoluble materials, and deposit of materials made insoluble by the temperature difference between the fluid and heat exchanger wall.

One source of fouling is carryover of brine and solids from a desalter, which will adversely affect downstream equipment. Typically, in a refinery, raw crude oil arrives containing water and salt. Part of the salts contained in the crude oil, particularly magnesium chloride, are hydrolysable at temperatures above 120° C. Upon hydrolysis, the chlorides are converted into hydrochloric acid, which can migrate to the overhead portion of the distillation column and corrode the condensers. To remove the salts, the crude oil is first treated in a desalter. The desalter is a large vessel full of liquid that uses an electric field to separate the crude oil from the water droplets. As it operates best at 120-150° C., it is generally placed within the preheat train. Downstream of the desalter, the crude oil is further heated in heat exchangers, as is known.

Desalters also help to remove insoluble salts and other solids that are often found in raw crude. Corrosion byproducts, such as iron sulfides, are often found in crude oil and may originate from crude oil pipelines, tanker holds and crude storage tankage. Larger particles will settle to some degree during desalting, whereas finer particles may not. The latter are known to contribute to fouling of crude preheat exchangers. Chemical additives, such as flocculants, are often added to desalters to enhance solids removal.

The impact of desalter upsets on downstream heat exchangers is a known problem. The aqueous brine, which contains dissolved salts such as sodium chloride, when carried-over with the desalted oil leads to fouling in the crude preheat exchangers and can contribute to overhead corrosion in the pipestill itself. Desalter upsets, such as brine carryover, can also pass more solids to downstream equipment.

Another source of fouling is asphaltene precipitation due to blending of incompatible crude oils. Most refineries run blends of different crude oils and care must be taken in blending of these crudes to avoid the unwanted precipitation of asphaltenic materials. Though guidelines are available to assist refinery operators to avoid this situation, it occurs nonetheless, with subsequent heat exchanger fouling.

Once heat exchangers are fouled, they must be cleaned to remove the deposits. Otherwise, foulant deposits reduce the heat transfer efficiency, which requires higher fuel consumption in downstream atmospheric pipestill furnaces. Cleaning typically involves removing the heat exchangers from service and hydroblasting the surfaces or otherwise cleaning the surfaces to remove the deposits. The equipment must then be brought back on-line. The frequency of required cleaning is driven by the amount of desalter upsets and asphaltene precipitation occurring in the equipment.

Mitigating or possibly eliminating fouling of heat exchangers can result in huge cost savings in reduced energy usage. Reduction in fouling also increases throughput and reduces maintenance and cleaning expenses.

Currently, desalter performance is not monitored. Most particulate monitoring methods rely on light transmittance to detect particles in fluid streams. However, due to the optical opacity of crude oil, these methods cannot be used. Other methods such as acoustic based methods are highly influenced by temperature and viscosity variations. Thus, in a refinery setting, these methods have a low level of reliability.

There is a need for monitoring the desalter performance, including the operation and output, especially in real-time and on-line. There is also a need for real-time on-line monitoring of incompatibility-induced asphaltene precipitation during crude blending.

BRIEF SUMMARY OF THE INVENTION

Aspects of embodiments of the invention relate to optimizing operations in a processing facility to mitigate fouling of heat exchange equipment.

Another aspect of embodiments of the invention relates to monitoring operation of desalter equipment on-line and in real-time to obtain data that can be used to optimize operations.

The invention is directed to a process for optimizing a refining operation to mitigate fouling of heat exchangers, comprising processing raw crude oil in a desalter with wash water to remove particles, soluble salts, and insoluble materials from the crude oil, measuring particles in the processed crude oil and generating data based on the measurements, and adjusting the processing based on the data generated from the measurements. The term "particles" in this context can include any second immiscible phase found in the crude oil such as salt brine droplets, insoluble inorganic salts, solid corrosion byproducts, mineral materials such as clays and aluminosilicates and asphaltenes for example. Ideally, one would like to measure the crude oil that is coming into the desalter and exiting the desalter and adjusting the operation of the desalter to maximize removal of brine, solids and asphaltenes. Operating parameters such as crude inlet temperature, electrostatic grid voltage, crude/water mixing energy, water addition rate, pH of water, rate of additives to assist flocculation could all be varied depending upon observed performance.

The process can include counting total particles, collecting the total particle counts and sorting the counts based on particle size. Preferably, the method of measuring the particles includes using focused beam reflectance.

The invention is additionally directed to a process for monitoring aqueous breakthrough in a stream of crude oil, comprising providing a stream of crude oil from an oil reserve, processing the stream of crude oil in a dewatering unit to reduce an amount of process water in the stream of crude oil, monitoring aqueous breakthrough during the processing in real time, controlling the processing based on the monitored aqueous breakthrough, and distributing the processed stream of crude oil for transport to a refining facility.

The invention is also directed to a process for evaluating components of a stream of crude oil in a refining operation, comprising providing a stream of crude oil for processing, measuring particles in the stream of crude oil by determining the size of the particles, and identifying the measured particles in the stream of crude oil.

Using the process, the stream of crude oil can be a desalted crude oil or a blend of at least two incompatible crude oils. Determining the size of the particles can include using focused beam reflectance.

The invention is also directed to a desalter for use in a refining operation, comprising a raw crude oil input, a wash water input in fluid communication with the raw crude oil input, including a mixer that mixes the raw crude oil with the wash water, and a vessel in fluid communication with the raw crude oil input that receives the raw crude oil and wash water mixture and a desalting mechanism connected to the vessel that operates on the mixture to dissolve salts from the mixture, to separate solids, and to separate the crude oil from the water. The desalter further comprises a desalted crude oil output in fluid communication with the vessel for discharging desalted crude oil for processing, a waste water output in fluid communication with the vessel for discharging waste water, and at least one sensor connected to the output that measures particles and droplets in the desalted crude oil output and generates data based on the measurement. Other additives to enhance desalter performance such as coalescing and flocculation aids may also be added to either or both the water or crude oil during the desalting process.

Preferably, the sensor is a particle measurement device including a focused beam reflectance device. An additional sensor can be connected to the vessel that measures particles and droplets in the mixture in the vessel. A controller can be connected to the sensor for receiving the data generated by the sensor and generating instructions based on the data. The desalter can be in combination with a refining facility.

These and other aspects of the invention will become apparent when taken in conjunction with the detailed description and appended drawings.

BRIEF DESCRIPTION OF THE DRAWINGS

The invention will now be described in conjunction with the accompanying drawings in which.

In the drawings, like reference numerals indicate corresponding parts in the different figures.

DETAILED DESCRIPTION OF PREFERRED EMBODIMENTS

This invention is directed to a method of mitigating fouling, in general. In a preferred use, the method and devices are applied to heat exchangers used in refining processes, such as in refineries or petrochemical processing plants. The invention is particularly suited for use in the crude pre-heat train equipment, in combination with a desalter, but is also useful for other heat exchangers and other processing equipment. Additionally, the invention can be used in pipestills (crude units), cokers, visbreakers, and the like. Of course, it is possible to apply the invention to other processing facilities and to other heat exchangers, particularly those that are susceptible to fouling in a similar manner as experienced during refining processes and are inconvenient to take off-line for repair and cleaning.

This invention is based on the recognition that it is desirable to eliminate or reduce fouling mechanisms in-process to prevent or minimize fouling. Moreover, the inventors recognize that it is desirable to take corrective action when carry-over of aqueous brine and solids and/or precipitation of solids happens before extensive downstream fouling occurs. Such intervention can mitigate fouling and avoid the associated costs of cleaning fouled equipment.

In accordance with this invention, the process involves monitoring the operation of a desalter in a processing facility. The operation of a desalter and the related processes are well known and are not discussed in detail except as it relates to the process invention described herein.

Figure 1:
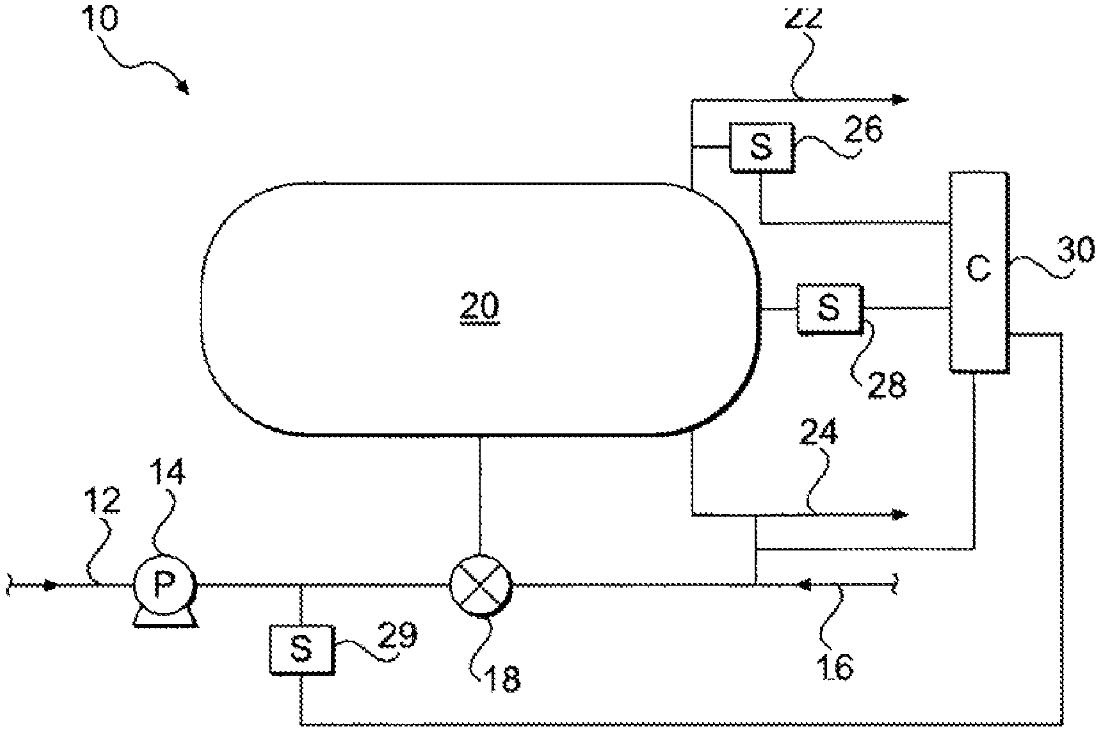
FIG. 1 is a schematic drawing of desalter equipment in a processing facility in accordance with this invention.

FIG. 1 shows a basic schematic of a desalter 10. As is known, raw crude oil is supplied to the process through a supply pipeline 12 and typically arrives containing water, salts, and other solids. It is fed to a desalter to remove the soluble salts and some solids by being pumped via a pump 14 to a desalting vessel 20. Upstream of vessel 20, the stream of raw crude oil is mixed with a stream of water 16 via a mixing valve 18 and the mixture is delivered to the vessel 20. Other additives to enhance desalter performance, such as coalescing and flocculation aids, may also be added to either or both the water and/or crude oil during the desalting process.

In the desalter vessel 20, typically an electric field is used to separate the crude oil from the water containing the dissolved salts. Some insoluble solids, especially larger particles will settle and accumulate at the bottom of the vessel 20 and are removed periodically through ports on the bottom of the vessel (not illustrated). Likewise, fine particulate materials are often found at the interface of the oil and brine layers in vessel 20 and can be removed periodically as this "rag layer" accumulates. This can be accomplished by use of ports as well, not illustrated in the figure. The desalted crude oil is output via a pipeline 22 to continue the processing. The water with the dissolved salts is drained from the vessel 20 via a drainage passage 24.

A known problem that occurs with desalting is that the desalted oil can carry over aqueous brine, which contains dissolved salts such as sodium chloride, and other solids. Carry-over can lead to fouling of downstream heat exchange equipment, particularly the crude oil preheat exchangers, and can contribute to overhead corrosion of the pipestill.

Figure 2:
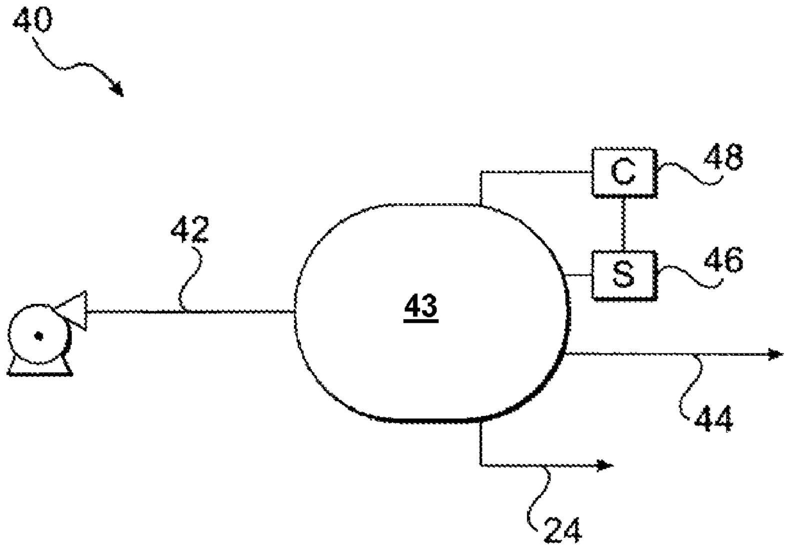
FIG. 2 is a schematic drawing of a dewatering unit in accordance with this invention.

FIG. 2 is a schematic diagram of the invention in use in an upstream operation in petrochemical processing, such as a dehydration or dewatering system 40. In this case, a stream of crude oil 42 obtained from an oil reserve by pumping is treated prior to shipping or transport via a pipeline 43 in a dewatering or dehydration unit 44. The crude is treated in the dewatering unit 44 to reduce the amount of process water in the crude. Aqueous breakthrough can be monitored in real time in the dewatering unit by a sensor 46, as described above, using focused beam reflectance measurement of particles. The unit 44 can then be optimized via a control mechanism 48. As this system is upstream and used at the initial phase of processing, optimization of this process would provide benefits that would translate throughout the treatment process.

Ideally, crude oil entering and exiting the desalter could be measured and then the operation of the desalter could be optimized to maximize removal of brine, solids, and asphaltenes. Operating parameters, such as crude inlet temperature, electrostatic grid voltage, crude/water mixing energy, water addition rate, pH of water, and rate of additives to assist flocculation, could all be varied depending on the observed performance.

The sensor or sensors 26, 28, 29 can be one or more measurement instruments used to measure particles and droplets in the crude oil in-process and in real-time. Particles, in this context, can include any second immiscible phase found in the crude oil, such as salt brine droplets, insoluble inorganic salts, solid corrosion byproducts, mineral materials, such as clays and aluminosilicates, and asphaltenes, for example. The instrument should be suitable for measuring any solids or dispersed-phase concentrations in process and in real-time. One suitable instrument that is commercially available is the Lasentec® Focused Beam Reflectance Measuring (FBRM®) instrument made by Mettler Toledo.

The Lasentec® FBRM® collects total particle counts and can simultaneously sort the total counts into "chord lengths" that relate to the size of the particles counted. Thus, increases in certain sizes of particles can be distinguished. This assists in distinguishing between brine breakthrough (represented as large droplets) and corrosion byproducts (represented as fine particles). FBRM® is also available in a video version that would enable an operator to visually see what is being counted as a "particle." This would make it apparent when second liquid phase droplets are being detected in contrast to solid particles.

In accordance with the process of this invention, the desalted crude oil output from the vessel 20 is detected using sensor 26 by collecting total particle counts and sorting the total counts into chord lengths that relate to the particles counted. By this, increases in certain sizes of particles can be distinguished. This allows particles to be identified. For example, brine breakthrough can be evidenced by large droplets, while corrosion by-products can be evidenced by fine particles. If a video enhanced measuring instrument is used, the particles being counted can be seen, which allows second liquid phase particles to be readily recognized. The data collected by the sensor is then provided to an operator or controller to take corrective action as explained above. This allows action to be taken when carry-over occurs but before fouling occurs.

The sensor 28 can also be used to monitor droplet size distribution of water added and mixed with the crude oil as part of the desalting operation. In this case, the mixture can be sampled and data can be gathered regarding the aqueous phase. Then, the operation can be adjusted before the desalted oil is output. For example, if the dispersed aqueous phase is too fine, brine carry-over can occur because the droplets will take too long to coalesce in the desalter. When a dispersion is too coarse or when insufficient mixing energy is provided, carry over of brine droplets can occur in which the brine droplets are encrusted with an organic and mineral coating that prevents their disruption and subsequent coalescence with the wash water. Fine tuning of the wash water and crude mixing can then be accomplished, which will enhance the desalter performance in general.

FIG. 2 is a schematic diagram of the invention in use in an upstream operation in petrochemical processing, such as a dehydration or dewatering system 40. In this case, a stream of crude oil 42 obtained from an oil reserve by pumping is treated prior to shipping or transport via a pipeline 44 in a dewatering or dehydration unit 44. The crude is treated in the dewatering unit 44 to reduce the amount of process water in the crude. Aqueous breakthrough can be monitored in real time in the dewatering unit by a sensor 46, as described above, using focused beam reflectance measurement of particles. The unit 44 can then be optimized via a control mechanism 48. As this system is upstream and used at the initial phase of processing, optimization of this process would provide benefits that would translate throughout the treatment process.

Another use for the process in accordance with this invention in which a measuring instrument is used to detect particle size is to optimize crude oil blending. Asphaltenes that separate as a second phase when incompatible crude oils are blended can be detected to monitor the blending in real-time and avoid subsequent fouling due to the incompatibility. Closer approach to compatibility limits can be achieved if a method to detect the onset of asphaltene precipitation is used in real-time monitoring.

This invention could also be used in other high fouling streams, such as in a fluidized bed catalytic cracking (FCC) cat slurry stream, which has a high solids content. The measuring system of this invention would enable particle measurement and real-time feedback for system optimization.

The following experiments were conducted to show that the process described above can detect brine and solids in crude oil.

Experiment 1

Figure 3:
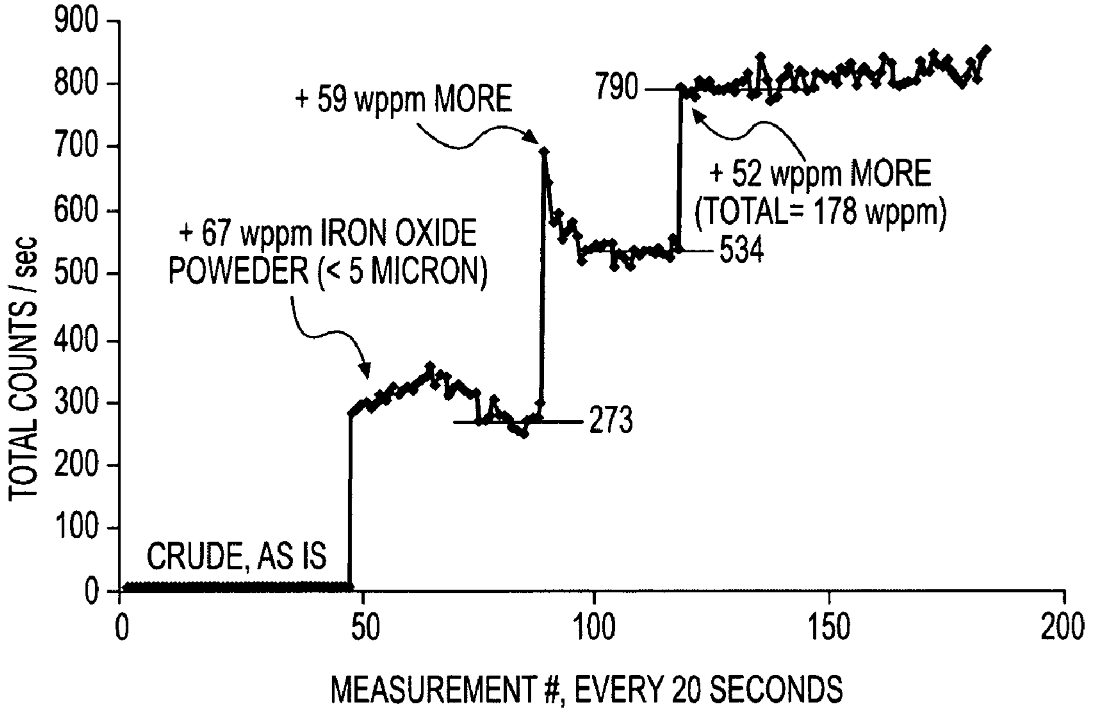
FIG. 3 is a graph showing the total particle counts detected by a sensor in accordance with this invention in crude oil following the addition of several aliquots of fine iron oxide powder.
Figure 4:
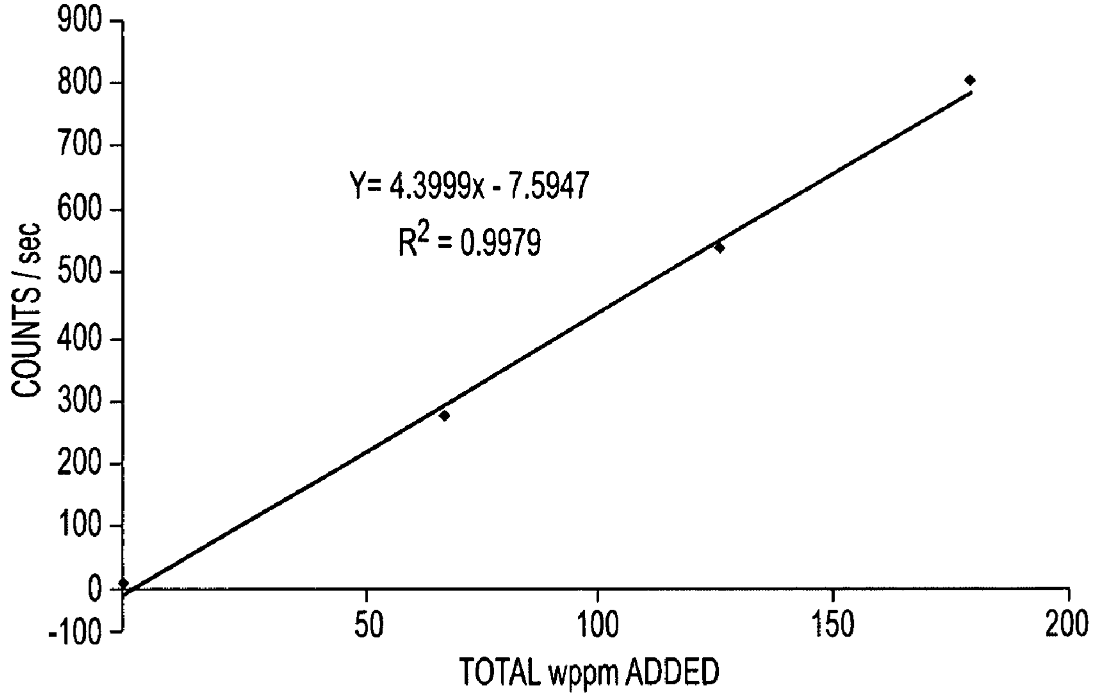
FIG. 4 is a graph showing the relation between total particle counts per second and the amount of solid iron oxide added.

To demonstrate that fine solid particles at the 50 wppm concentration level in crude oil can be detected, an experiment using the Lasentec® FBRM® was used. Two hundred mls of whole crude oil was poured into a glass beaker. This beaker was then positioned in the Lasentec® fixed beaker stand that holds the Lasentec® probe in an optimal position within the beaker in relation to a variable speed, four blade propeller stirrer that circulates the test solution past the probe window. The measurements were conducted at ambient temperature. After an initial total particle count was obtained with the instrument, data collection was halted. Then, about 10 mgs of iron oxide powder (Aldrich, <5 micron) was added to the crude oil in the beaker. The stirring rate was increased to 1000 rpm for 1 minute to fully disperse the solid, and the data collection was resumed. A significant increase in the number of particle counts was observed. This procedure was repeated for two more additions of solids. The results are shown in FIG. 3. As seen in FIG. 3, the total count/sec at each increment of solids addition is represented by a plateau. FIG. 4 shows a plot of the correlation between total counts/sec measured by the Lasentec® FBRM® and the amount of solid added to the crude. As can be appreciated from the graph, there is strong linear correlation with an $r^2$=0.998.

Experiment 2

Figure 5:
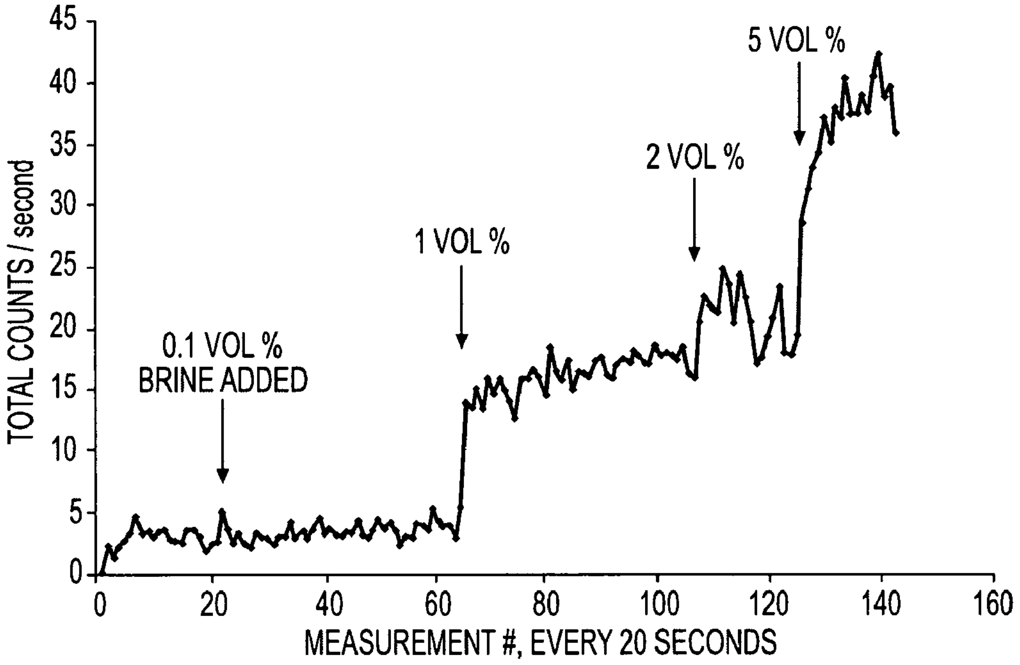
FIG. 5 is a graph showing the total particle counts detected by the sensor in accordance with this invention in crude oil following the addition of several aliquots of brine.

A second experiment was conducted to demonstrate that brine dispersed in crude oil can be detected. The experiment used the Lasentec® FBRM® with the same experimental set up and procedure as in the first experiment, described above, except that aliquots of a 20 weight % sodium chloride in water solution was added rather than the addition of aliquots of solid iron oxide. The first addition represented 0.1 volume %, and no change in total particle counts was recorded. For the FBRM®, “particles” can be solid particles, gas bubbles, or dispersed second liquid phases, such as brine droplets, as in this case. Upon addition of 1 volume % of brine, a significant jump in signal was observed. Additional increases of 2 volume % and 5 volume % also produced increases in particle counts, but not in a linear fashion, as in the first experiment. This may be due to the unstable nature of the dispersion that is produced by the addition of brine droplets, as brine droplets will coalesce with each other over time and stick to glass beaker walls. It may be necessary to add a dispersing agent to stabilize the aqueous dispersion and form a stable emulsion to test the lower detection limits for brine in oil using the FBRM®. The data obtained in the experiment is shown in the graph of FIG. 5. This experiment suggests that at least 1 volume % carryover of brine in crude oil can be measured. The formation of stable emulsions in the desalter is one of the types of upsets that this method can readily detect.

Experiment 3

Figure 6:
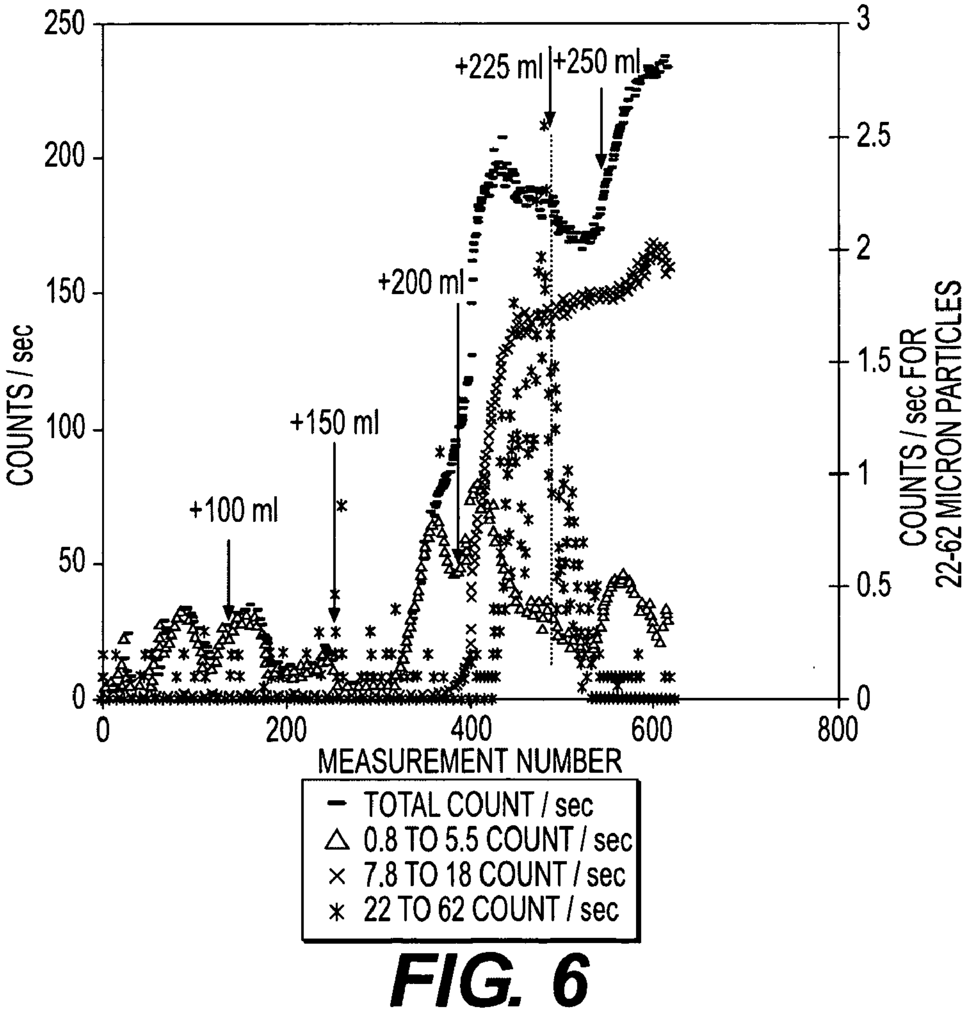
FIG. 6 is a graph showing the total particle counts detected by the sensor in accordance with this invention during the course of blending two incompatible crude oils.

In a third experiment, the FBRM® probe was used to detect the formation of asphaltenes during the course of the blending of two incompatible crude oils. Initially, 250 mls of a crude oil was stirred at room temperature, and the probe was used to measure the background particle content. At room temperature, wax crystallites in the crude oil were evident by eye and produced a noisy baseline to the FBRM®, as seen in FIG. 6. After an addition of 150 mls of n-heptane, most of the wax crystals appeared to dissolve, and the total particle count dropped to a steady low level. Upon addition of 50 mls more of heptane, the particle count increased dramatically. Initially, this growth was limited to the smaller particles in the 0.8 and 5.5 micron chord length range. Then, the particles grew progressively larger. As indicated in FIG. 6, the Lasentec® FBRM® was used to detect the “titration-like” response at the point of asphaltene phase separation. The absence and presence of asphaltenes was confirmed by analysis of the test mixture under a light microscope. High particle counts correlated with the presence of asphaltenes under the microscope. This information is useful in determining incompatibility numbers in a laboratory setting and may be used in crude oil blending in the refinery to monitor for the occurrence of feed incompatibilities.

A follow up experiment was conducted in which asphaltene precipitation from one crude oil, Crude A, was induced by the addition of a second, incompatible crude oil, Crude B. The same titration-like response was obtained.

Thus, it can be appreciated from the results of these experiments that measuring particles and droplet size in crude oil can be effectively accomplished. As demonstrated, aqueous brine and iron oxide solids can be detected in crude oil by measuring particles using focused beam reflectance techniques. Using data generated from such measurements can be used in accordance with this invention to mitigate fouling by controlling desalter operations and output in real-time to prevent or minimize carry-over of aqueous brine and particles. The data can also be used in accordance with this invention to control blending during the mixing of incompatible crude oils to control the precipitation of asphaltenes.

It will be recognized by those of ordinary skill in the heat exchanger art that the invention can be applied to any heat exchanger surface in various types of known heat exchanger devices.

Various modifications can be made in the invention as described herein, and many different embodiments of the device and method can be made while remaining within the spirit and scope of the invention as defined in the claims without departing from such spirit and scope. It is intended that all matter contained in the accompanying specification shall be interpreted as illustrative only and not in a limiting sense.

What is claimed is:

1. A process for optimizing a petroleum desalting operation to mitigate fouling of equipment downstream of the desalting operation, comprising:

processing raw crude oil in a desalter with wash water;

measuring particles in the processed crude oil from the desalter by focused beam reflectance measurement;

collecting the total particle counts and sorting the counts based on particle size from the focused beam reflectance measurement;

generating data based on the counts;

distinguishing brine breakthrough from the desalter based on the generated data;

adjusting the processing in the desalter.

2. The process of claim 1, wherein measuring particles includes collecting the total particle count.

3. The process of claim 1, wherein sorting the counts based on particle size includes determining a chord length for the counted particles.

4. The process of claim 1, wherein generating data includes identifying the particles.

5. The process of claim 4, wherein the particles are identified as one of a plurality of carry-over particles including salts, aqueous brine, asphaltenes, clays, alumino-silicates and corrosion by-products.

6. The process of claim 1 in which the brine breakthrough from the desalter is made on the basis of relatively large droplets representing brine breakthrough being distinguished from relatively fine solid particles.

7. The process of claim 1, further comprising measuring particles in the raw crude oil at an inlet of the desalter prior to processing in the desalter.

8. The process of claim 1, wherein adjusting the processing in the desalter includes controlling at least one of the wash water rate, mixing energy with the crude oil, pH, and temperature.

9. The process of claim 1, wherein adjusting the processing in the desalter includes controlling addition rates of chemical additives to enhance flocculation of solids and dispersancy of asphaltenes.

10. The process of claim 1, wherein adjusting the processing in the desalter includes controlling the applied voltage applied to the electrostatic grids in the desalter.

11. A process for monitoring aqueous breakthrough in a stream of crude oil, comprising:

providing a stream of crude oil from an oil reserve;

processing the stream of crude oil in a dewatering unit to reduce an amount of process water in the stream of crude oil;

monitoring aqueous breakthrough during the processing in real time by measuring particles in the stream of crude oil by means of focused beam reflectance;

determining the size of the measured particles;

identifying the measured particles in the stream of crude oil;

controlling the processing in the dewatering unit based on the monitored aqueous breakthrough; and distributing the processed stream of crude oil for transport to a refining facility.

12. The process of claim 11, wherein the stream of crude oil is a blend of at least two crude oils.

13. The process of claim 11, wherein the size of the particles is determined by collecting total particle counts and sorting the total counts based on chord lengths of the measured particles.

14. A desalter for use in a refining operation, comprising:

a raw crude oil input;

a wash water input in fluid communication with the raw crude oil input, including a mixer that mixes the raw crude oil with the wash water;

a vessel in fluid communication with the raw crude oil input that receives the raw crude oil and wash water mixture to dissolve salts from the mixture, to separate solids, and to separate the crude oil from the water;

a desalted crude oil output in fluid communication with the vessel for discharging desalted crude oil for processing;

a waste water output in fluid communication with the vessel for discharging waste water; and at least one focused beam reflectance sensor connected to the desalted crude oil output configured to measure particles and droplets in the desalted crude oil output to generate data from total particle counts and counts based on particle and droplet sizes from the focused beam reflectance measurement for distinguishing brine breakthrough from the desalter.

15. A method of monitoring an oil blending process to detect the blending of incompatible oils that form asphaltene precipitates upon being blended, which comprises:

blending oil streams to form a blended oil stream;

monitoring the blended oil stream in real time by measuring particles in the blended oil stream by means of focused beam reflectance;

determining the size of the measured particles;

identifying the measured particles in the blended stream and identifying asphaltenes;

controlling the blending based on the monitored measured particles and identified asphaltenes.

16. The process of claim 15, wherein the blending is controlled by identifying the particles and identifying asphaltenes.

17. The process of claim 16, further comprising adjusting the blending based on compatibility.

18. The process of claim 15, wherein one stream is FCC cat slurry.

19. The process of claim 15 wherein the streams are crude oil streams.

* * * * *